Figure 6:
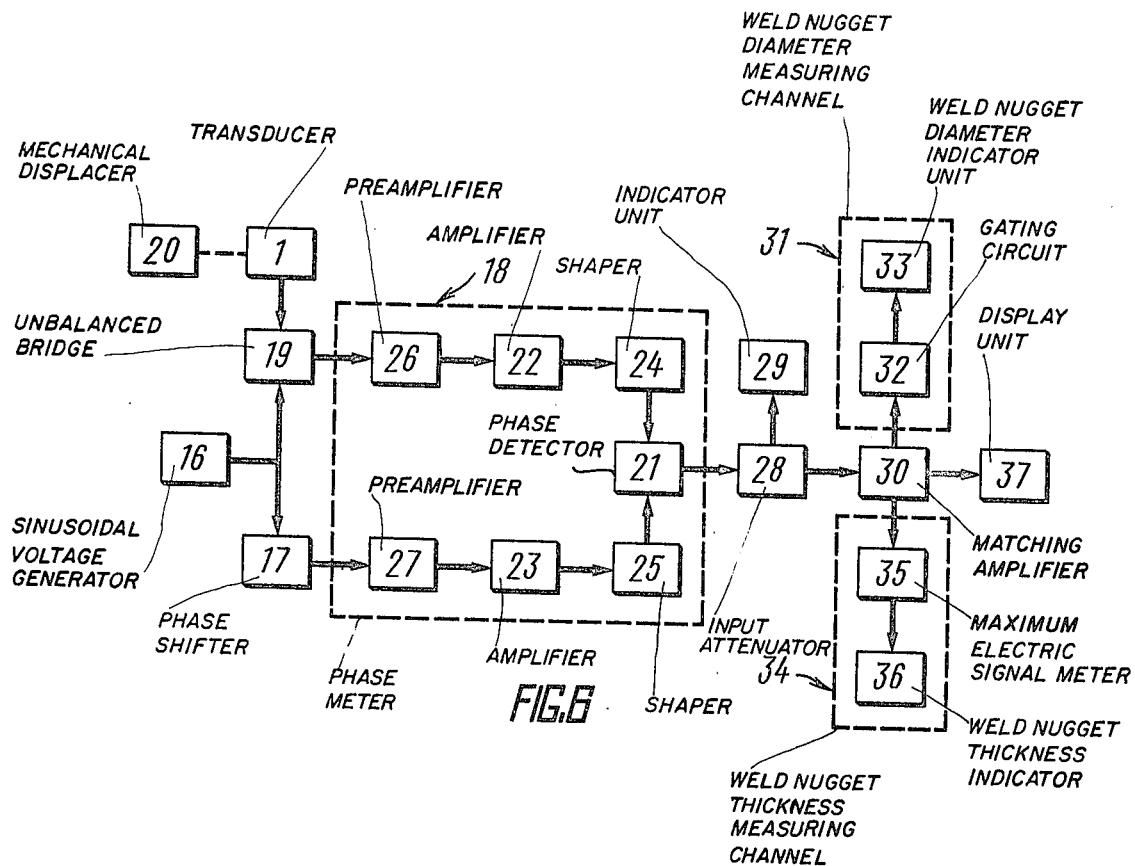

United States Patent [19]

Fastritsky et al.

[11] 4,287,474
[45] Sep. 1, 1981

[54] METHOD AND APPARATUS FOR NON-DESTRUCTIVE QUALITY TESTING OF SPOT WELDS

[76] Inventors: Viktor S. Fastritsky, ulitsa Michurina, 27, kv. 14; Pavel S. Fishkin, ulitsa Maskavas, 427, kv. 54; Evgeny P. Rybalkin, ulitsa Gorkogo, 78, kv. 2, all of Riga, U.S.S.R.

[21] Appl. No.: 11,546

[22] Filed: Feb. 12, 1979

[51] Int. Cl.$^3$ ............................................. G01R 33/12
[52] U.S. Cl. ..................................... 324/233; 324/229
[58] Field of Search ............... 324/228, 229, 233, 234, 324/236–240, 262

[56] References Cited

U.S. PATENT DOCUMENTS

| | | | |
|---|---|---|---|
| 2,764,734 | 9/1956 | Yates | 324/229 |
| 2,985,824 | 5/1961 | Renken | 324/233 |
| 3,302,105 | 1/1967 | Libby et al. | 324/233 |
| 3,526,829 | 9/1970 | Noble | 324/238 |
| 3,535,625 | 10/1970 | Pratt | 324/233 |
| 3,566,258 | 2/1971 | Mori et al. | 324/233 |
| 3,895,290 | 7/1975 | Audenard et al. | 324/233 |

FOREIGN PATENT DOCUMENTS 270260  8/1970  U.S.S.R. .................................. 324/229

Primary Examiner—Gerard R. Strecker
Attorney, Agent, or Firm—Lackenbach, Lilling & Siegel

[57] ABSTRACT

A method of non-destructive quality testing of spot welds resides in that in the test weld nugget region there is produced a primary electromagnetic field inducing eddy currents in that region. Thereupon, the primary electromagnetic field is displaced in a direction parallel to the surface of contact of the welded parts. The phase angle between the resultant and primary magnetic fields is measured at the points characterized by the maximum of the primary electromagnetic field intensity lying on the same line parallel to the surface of the test weld and located in the zone disposed between the points located on either side of the test weld zone wherein the weld nugget is disposed, the weld nugget thickness is evaluated from the difference between the maximum phase value of the intensity measured in the test weld zone wherein the weld nugget is absent and the minimum phase value of the intensity measured in the test weld zone wherein the weld nugget is disposed. The weld nugget diameter is evaluated from the length of the zone within the limits where the phase of the intensity has its minimum value. An apparatus for non-destructive quality testing of spot welds includes a sinusoidal voltage generator with a phase shifter and an unbalanced bridge circuit having a superimposed eddy current transducer included into one of its branches, which are connected to the output thereof, and the outputs of the phase shifter and unbalanced bridge circuit being connected with the respective inputs of a phase meter, the superimposed eddy current transducer being complete with an attachment for its mechanical displacement in the plane parallel to the surface of contact of welded parts.

5 Claims, 7 Drawing Figures

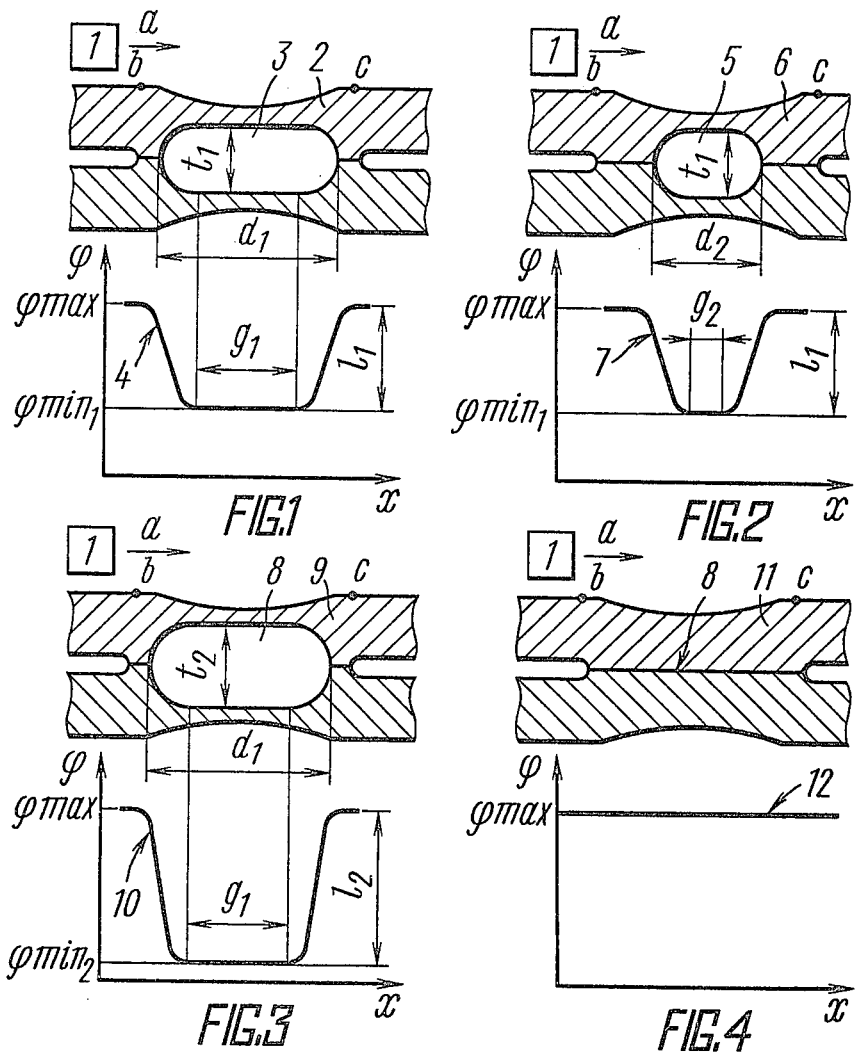

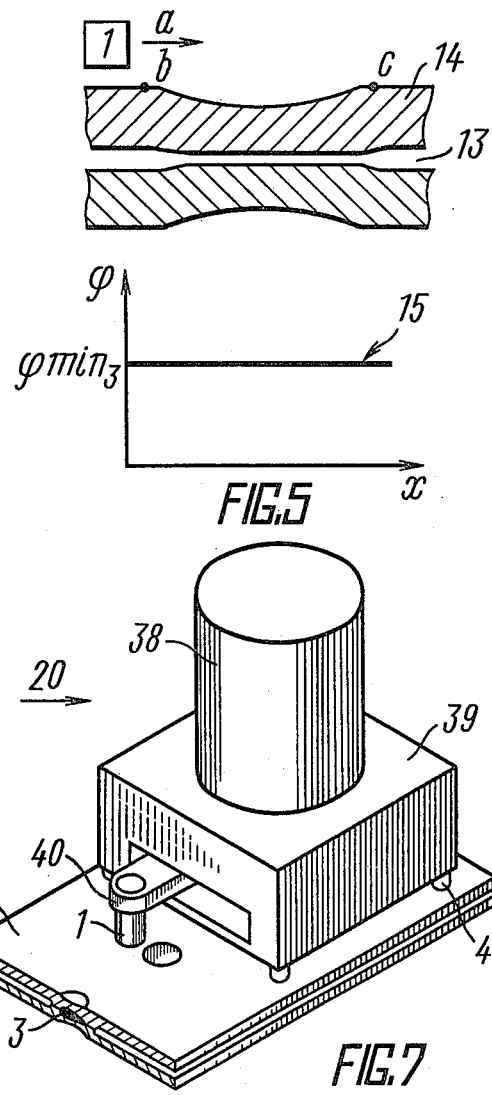

METHOD AND APPARATUS FOR NON-DESTRUCTIVE QUALITY TESTING OF SPOT WELDS

FIELD OF THE INVENTION

The present invention relates to the field of weld testing, and more particularly to methods and apparatus for non-destructive quality testing of spot welds.

The present invention can be most advantageously used in the machine and aviation industries for non-destructive testing of variations in the properties of the material of various metal articles.

BACKGROUND OF THE INVENTION

Spot welding is one of the most widespread methods of connecting parts. For example, a Boeing 747 plane has over 300,000 spot welds. However, the use of spot welding in vital constructions without a reliable method and apparatus for testing the parameters of the nugget in a spot weld is impossible during welding as well as under working conditions in finished articles.

Known in the art is a method of non-destructive quality testing of spot welds (cf. a book by L. S. Feldman "Non-destructive Quality Testing of Glue-Welded Joints", "Tekhnika" Kiev, 1973), residing in that longitudinal ultrasonic oscillations are directed into the cast region at an angle to the surface of the test weld. Thereupon, an ultrasonic detector is displaced over the test weld. If the ultrasonic detector is situated over the zone of the test weld wherein the weld nugget is absent, in this case at the measuring device, there will appear a signal reflected from the contact surface of the welded parts. If the ultrasonic detector is situated over the zone of the test weld wherein the weld nugget is located, in this case the reflected signal will disappear. The diameter of the weld nugget is evaluated by measuring the distance between the points corresponding to disappearance and appearance of the reflected signal.

The apparatus realizing this method of non-destructive quality testing of spot welds comprises a master oscillator having a pulse generator connected to one of the outputs thereof and a sweep generator connected to another output. The output of the pulse generator is connected with the ultrasonic detector through a pulse amplifier. Connected to the outputs of the sweep generator and of the ultrasonic detector is a cathode-ray tube.

The master oscillator generates oscillations energizing the pulse generator and the sweep generator. From the pulse generator, high frequency electric pulses are supplied through the pulse amplifier to the ultrasonic detector and generate therein ultrasonic oscillations. These oscillations are applied to the test weld. In the absence of a weld nugget and with an air clearance between the welded parts, ultrasonic waves are reflected from the interface of the mediums and a signal is returned to the detector which is supplied to the cathode-ray tube controlled by the sweep generator. With a weld nugget present, ultrasonic oscillations pass through the fusion zone without any reflection.

Displacing the ultrasonic detector over the test weld, an instant of disappearance and appearance of the reflected signal on the face of the cathode-ray tube is recorded. The diameter of the test weld nugget is determined by measuring the distance between the points on the face of the cathode-ray tube, corresponding to instants of disappearance and appearance of the reflected signal.

The disadvantage of the aforementioned method and apparatus for non-destructive quality testing of spot welds is that, when there is an absence of a clearance between the welded parts with a poor fusion in the form of adhesion, a reflected signal is not produced. Moreover, for a number of materials using this method it is impossible to detect poor fusion in the form of adhesion which is one of the most dangerous welding defects.

For a number of materials having inhomogeneity of chemical composition in the weld nugget, poor fusion can be detected by means of a radio-graphic method.

Known in the art is a method of non-destructive quality testing of spot welds, wherein X-rays non-uniformly absorbed by various nugget regions because of inhomogeneity of chemical composition of the weld nugget are directed onto the test weld. X-rays pass through the test weld and fall onto the X-ray film whereon, after development, liquation rings are formed, the diameter of the weld nugget being evaluated according to the ring dimensions.

The apparatus realizing this method of non-destructive quality testing of spot welds comprises an X-ray source and a detector, such as an X-ray film, whereon the X-rays having passed through the tested weldment are recorded.

The disadvantage of the aforementioned method and apparatus for non-destructive quality testing of spot welds is that it is impossible to determine the nugget thickness because X-raying the tested material in a single plane. Besides, for materials which do not exhibit sharply defined inhomogeneity of chemical composition in the weld nugget section, it is also impossible to determine the diameter of the weld nugget, i.e. to detect such a dangerous and popular welding defect as poor fusion.

To ensure radio-graphic quality testing of spot welds formed of the materials which do not exhibit sharply defined inhomogeneity of chemical composition in the weld nugget section, so-called X-ray contrast materials are used which are introduced between the welded parts prior to welding and make it possible to obtain a contrast image of the weld nugget on the X-ray pattern. However, the use of X-ray contrast materials complicates the testing process which in turn results in a decrease of efficiency and in an increase of a testing cost price.

It is possible to increase the efficiency of the method and to decrease the equipment cost price by the use of an eddy current testing method which depends upon the fact that the nugget of the test weld and the welded material outside the nugget region have various values of electric conductivity.

Known in the art is a method of non-destructive quality testing of spot welds (cf. USSR Inventor's Certificate No. 336,587), wherein eddy currents are induced in the test weld nugget region which produce a secondary electromagnetic field in the weld zone. The electromagnetic field of eddy currents acts on the transducer varying its output signal according to the weld properties. The dimensions of the weld nugget are evaluated by measuring the output signal of the eddy current transducer.

The apparatus realizing this method of non-destructive quality testing of spot welds comprises a low frequency generator, a T-shaped LCR bridge connected to the output thereof, a main eddy current transducer included in the T-shaped bridge as an L-element, an electronic indicator of the bridge output signal, a phase shifter, frequency multipliers and a phase meter which are connected between the output of the generator and the main eddy current transducer.

Fixed in the center of the main eddy current transducer is an additional eddy current transducer which forms in conjunction with a capacitor a measuring circuit intended to test the depth of indentation. The measuring circuit of the additional eddy current transducer is connected to the high frequency generator and to the indentation depth indicator.

From the low frequency generator a sinusoidal voltage is applied to the input of the T-shaped symmetric bridge and to the phase shifter. The bridge is balanced when the transducer is placed on the reference comparison weldment. Thereupon, the transducer having the parameters which vary according to the weld quality, is placed on the test weld, and an unbalance signal dependent on the weld quality appears at the bridge output. The amplitude of the unbalance signal is measured by the electronic indicator. To measure the phase, the signal is taken directly from the main eddy current transducer and applied to the phase meter through the frequency multiplier. A reference voltage is supplied from the low frequency generator to the phase meter through the phase shifter and frequency multiplier. A voltage to the measuring circuit of the depth of indentation is supplied from a high frequency generator. The signal corresponding to the depth of indentation is supplied from the measuring circuit to the indentation depth indicator. The weld quality is evaluated according to the obtained values of the signal amplitude and phase.

The disadvantage of the aforementioned method and apparatus for non-destructive quality testing of spot welds is that, because of the use of two eddy current transducers disposed coaxially, overall dimensions of the detecting element are considerably increased and therefore it is impossible to test welds of small thickness.

Known in the art is a method of non-destructive quality testing of spot welds (cf. U.S. Pat. No. 3,526,829) characterized in that two pulsed electromagnetic fields are produced one of which is applied to the test weld and another is applied to the reference weld. Thereupon, the depth of penetration of two pulsed electromagnetic fields into the welds is measured by dynamic impedance measurement of the effect of the induced eddy currents on their applied electromagnetic fields.

The apparatus realizing this method of non-destructive quality testing of spot welds comprises eddy current transducers placed onto the reference and test welds, an impedance comparator unit having its inputs connected with the eddy current transducers, and a controlled switch having its output connected with a stored energy source. The output of the comparator unit is connected with a threshold circuit having its output connected with an information display unit wherein an information signal varying in accordance with any difference between the measured impedance values in the reference weld and the test weld is displayed in an acceptance-rejection form.

By means of this method and apparatus, it is possible to test spot welds of small thickness.

The disadvantage of the aformentioned method and apparatus for non-destructive quality testing of spot welds is that they provide quality testing of spot welds only in ferromagnetic materials.

Known in the art is a method of non-destructive quality testing of spot welds (cf. a paper "Apparatus for Quality Testing of Spot Welding of Aluminium Alloys" by V. S. Fastritsky, E. P. Rybalkina, and P. Sh. Fishkin in the book "Methods and Apparatus for Automatic Testing", issue 13, p.p. 18–24, Riga, 1975), characterized in that in the test weld zone a primary electromagnetic field is produced which induces in this zone eddy currents producing a secondary field, whereupon the phase value of the resultant electromagnetic field intensity is determined according to which the presence and quality of the nugget in a spot weld are evaluated.

The apparatus realizing this method of non-destructive quality testing of spot welds comprises a sinusoidal voltage generator, a reference channel connected to one of the outputs thereof and representing a phase shifter having its output connected to one of the inputs of a phase meter, and a measuring channel connected to another output of the generator and representing an unbalanced bridge circuit with a superimposed eddy current transducer included into one of its branches and with its output connected to another input of the phase meter.

The voltage from the sinusoidal voltage generator is supplied to the phase shifter which serves to set the phase of the reference voltage, and to the bridge circuit with one of its branches including the eddy current transducer placed upon the test weld. The transducer impedance resistance, and hence the output signal of the bridge circuit wherein it is included, vary according to the weld quality. The bridge circuit is adjusted so that the phase of the output voltage is not dependent upon the size of the clearance between the transducer and the weldment, but is determined only by variations in the electric conductivity of the tested zone, which in turn is dependent upon the weld quality. From the output of the phase shifter the signal is applied to one of the inputs of the phase meter, and from the output of the bridge circuit it is fed to the second input of the phase meter. Placing the transducer upon the reference weld, the phase of the reference voltage is varied by the phase shifter so that the phase shift between the reference and measured voltages in case of a quality weld should be equal to zero. Thereupon, the transducer is placed onto the test weld, and the weld quality is determined according to indications of the phase meter.

The disadvantage of the aforementioned method of and apparatus for non-destructive quality testing of spot welds is that the output signal of the transducer contains only the resultant information on the dimensions of the weld nugget and on presence of defects therein with the result that in some cases wrong results of the weld quality evaluation may be obtained. For example, with the reduced dimensions of the weld nugget and with cracks present therein, the signal obtained at the output of the apparatus can be the same as for a quality weld nugget. A similar result can be obtained for a complete infusion with a clerance between welded parts. This disadvantage also restricts possible control of welding conditions because of lack of data on the weld nugget diameter and thickness.

Besides, the apparatus should be previously adjusted by placing the superimposed eddy current transducer upon the reference weld. However, for a number of materials, such as aluminium-magnesium alloys, a reference weld can not be defined by non-destructive methods.

Thus, eddy current methods of and apparatus for non-destructive quality testing of spot welds make it possible to obtain a summary characteristic of a spot weld dependent upon variations in the whole volume of the weld nugget without differentiating the effect of variations in the diameter and thickness of the spot weld.

Such characteristic of a spot weld does not allow for reliable testing of weldments with different thicknesses and of weldments formed of composite alloys.

SUMMARY OF THE INVENTION

It is an object of the present invention to eliminate the aforementioned disadvantages.

Another object of the present invention is to increase accuracy and reliablility of testing.

Still another object of the present invention is to provide a method and apparatus for non-destructive quality testing of spot welds making it possible to perform separate tests of the diameter and thickness of a weld nugget.

A further object of the present invention is to provide a method and apparatus for non-destructive quality testing of spot welds, making it possible to perform tests without previous adjustment on a reference weld.

Yet another object of the present invention is to provide a method and apparatus for non-destructive quality testing of spot welds making it possible to perform tests regardless of variations in the material chemical composition and environmental conditions, such as an ambient temperature.

With these and other objects in view, there is provided a method of non-destructive quality testing of spot welds by producing in a test weld nugget region a primary electromagnetic field inducing eddy currents in said region and by determining in this region the phase value of a resultant electromagnetic field intensity, whereby presence and quality of the weld nugget are evaluated, wherein according to the invention, the primary electromagnetic field is displaced in the direction parallel to the surface of contact of welded parts, and the phase angle between the resultant and primary magnetic fields is measured at the points characterized by the maximum of the primary electromagnetic field intensity and lying on the same line parallel to the surface of the test weld of the nugget region in the zone disposed between the points located on either side of the test weld zone wherein the weld nugget is disposed, the weld nugget thickness being evaluated from the difference between the maximum phase value of the intensity measured in the test weld zone wherein the weld nugget is absent and by the minimum phase value of the intensity measured in the test weld zone wherein the weld nugget is disposed, while the weld nugget diameter is evaluated from the length of the zone within the limits whereof the phase of the intensity has its minimum value.

Displacement of the primary electromagnetic field in the direction parallel to the surface of contact of welded parts makes it possible to induce eddy currents and to measure the phase angle between the resultant and primary magnetic fields in test weld zones having different electric conductivity.

With these and other objects in view, there is also provided an apparatus for non-destructive quality testing of spot welds to realize the method, comprising a sinusoidal voltage generator having an output connected both to a reference channel including a phase shifter, and to a measuring channel including an unbalanced bridge circuit with a superimposed eddy current transducer included into one of the branches thereof, the outputs of the phase shifter and unbalanced bridge circuit being connected with respective inputs of a phase meter, wherein, according to the invention, the superimposed eddy current transducer is provided with an attachment for its mechanical displacement in the plane parallel to the surface of contact of welded parts.

Completing the superimposed eddy current transducer with the attachment for its mechanical displacement provides movement of said transducer over the test weld zone wherein the weld nugget is disposed and over the zone wherein the weld nugget is absent, i.e. the superimposed eddy current transducer travels over the zones having different electric conductivities.

These and other objects and advantages of the present invention will become more apparent upon consideration of the following detailed description of its embodiments taken in conjunction with the accompanying drawings in which:

FIG. 1 schematically shows a cross sectional view of a spot weld with a superimposed eddy current transducer placed thereabove, and a curve representing the output signal of the superimposed eddy current transducer versus its position with respect to the weld, according to the invention;

FIG. 2 schematically shows a cross sectional view of one of the forms of a spot weld with a superimposed eddy current transducer placed thereabove, and a curve representing the output signal of the superimposed eddy current transducer versus its position with respect to the weld, according to the invention;

FIG. 3 schematically shows a cross sectional view of another form of a spot weld with a superimposed eddy current transducer placed thereabove, and a curve representing the output signal of the superimposed eddy current transducer versus its position with respect to the weld, according to the invention;

FIG. 4 schematically shows a cross sectional view of still other form of a spot weld with a superimposed eddy current transducer placed thereabove and a curve representing the output signal of the superimposed eddy current transducer versus its position with respect to the weld, according to the invention;

FIG. 5 schematically shows a cross sectional view of yet another form of a spot weld with a superimposed eddy current transducer placed thereabove and a curve representing the output signal of the superimposed eddy current transducer versus its position with respect to the weld, according to the invention;

FIG. 6 shows a block diagram of an apparatus realizing a method of non-destructive quality testing of spot welds, according to the invention; and FIG. 7 shows a perspective view of an attachment for mechanical displacement of the superimposed eddy current transducer, according to the invention.

A method of non-destructive quality testing of spot welds is realized as follows. A superimposed eddy current transducer 1 (FIG. 1) is placed over a test weld 2. To suppress the effect of variations in the clearance between the superimposed eddy current transducer 1 and the test weld 2, the superimposed eddy current transducer 1 is included into an unbalanced bridge circuit which is adjusted in accordance with the known method so that the phase of the output voltage of the unbalanced bridge circuit is not dependent upon the clearance between the superimposed eddy current transducer 1 and the test weld 2 and is determined only by variations in electric conductivity of a test zone which in turn is dependent upon variations in the material structure, i.e. upon the dimensions of the weld nugget and presence of defects therein.

By means of the superimposed eddy current transducer 1 powered by an alternating current, a primary electromagnetic field is produced which induces eddy currents in the test weld 2.

Eddy currents produce a secondary electromagnetic field which, interacting with the primary electromagnetic field, forms a resultant electromagnetic field having the magnitude and phase of intensity dependent upon the weld quality. The resultant electromagnetic field acts on the superimposed eddy current transducer 1 varying its parameters according to the weld quality.

The superimposed eddy current transducer 1 is displaced in the plane parallel to the surface of contact of the welded parts of the test weld 2 in the direction indicated by the arrow "a". In doing so, the phase angle between the resultant and primary magnetic fields will vary according to the position of the superimposed eddy current transducer 1.

The phase angle between the resultant and primary magnetic fields is measured at the points characterized by the maximum of the primary electromagnetic field intensity, i.e. at the points over which the superimposed eddy current transducer 1 is disposed as the measurements are being taken.

The points of measurement lie on the same line parallel to the surface of the test weld 2 in the zone disposed between the points labelled "b" and "c" which are located on either side of the zone of the test weld 2 wherein a weld nugget 3 is disposed. When the primary electromagnetic field is displaced over the zone of the test weld 2 and the weld nugget 3 is absent, the phase angle between the resultant and primary magnetic fields intensity at the points characterized by the maximum of the primary electromagnetic field intensity maintains its constant value. As the primary electromagnetic field approaches the zone of the test weld 2, wherein the weld nugget 3 is disposed, the phase angle between the resultant and primary magnetic fields at the points characterized by the maximum of the primary electromagnetic field intensity is decreased, the value by which the phase angle between the resultant and primary magnetic fields is decreased being dependent upon the thickness of the weld nugget 3. As the primary electromagnetic field is displaced along the zone of the test weld 2, wherein the weld nugget 3 is disposed, the phase angle between the resultant and primary magnetic fields at the points characterized by the maximum of the primary electromagnetic field intensity maintains its lower constant value. As the primary electromagnetic field is transferred from the zone of the test weld 2, wherein the weld nugget 3 is disposed to the zone of the test weld 2 wherein the weld nugget 3 is absent, the phase angle between the resultant and primary magnetic fields intensity at the points characterized by the maximum of the primary electromagnetic field intensity again increases up to its original value.

A curve 4 shown in FIG. 1 represents the phase angle between the resultant and primary magnetic fields intensity versus the position of the superimposed eddy current transducer 1 with respect to the test weld 2, the weld nugget 3 having a diameter "$d_1$" and thickness "$t_1$" corresponding to a quality weld, a distance X travelled by the superimposed eddy current transducer 1 being laid off along the abscissa and a phase $\phi$ of the resultant electromagnetic field intensity being laid off along the ordinate.

Referring to the curve 4, it could be seen that, if the superimposed eddy current transducer 1 is located over the test weld 2 where the weld nugget 3 is absent, the phase value of the resultant electromagnetic field intensity corresponds to the value $\phi_{max}$. If the superimposed eddy current transducer 1 is located over the weld nugget 3, the phase value of the resultant electromagnetic field intensity corresponds to the value $\phi_{min1}$. When the superimposed eddy current transducer 1 is displaced within the confines of the zone of the test weld 2 wherein the weld nugget 3 is disposed, the phase value of the resultant electromagnetic field intensity equal to $\phi_{min1}$ remains constant.

The difference between $\phi_{max}$ and $\phi_{min1}$ is labelled "$l_1$", and the thickness "$t_1$" of the weld nugget 3 is evaluated according thereto.

The distance within the limits wherein $\phi_{min1}$ has constant value is labelled "$g_1$", and the diameter "$d_1$" of the weld nugget 3 is evaluated according thereto.

FIG. 2 shows a form of a spot weld wherein a weld nugget 5 of a test weld 6 has a thickness "$t_1$" equal to the thickness of the weld nugget 3 (FIG. 1) of the test weld 2, and a diameter "$d_2$" smaller than the diameter "$d_1$" of the weld nugget 3 (FIG. 1) of the test weld 2.

When the superimposed eddy current transducer 1 (FIG. 2) is displaced in the direction indicated by the arrows "a" between the points labelled "b" and "c", the phase angle between the resultant and primary magnetic fields will vary according to a curve 7. Referring to the curve 7, it could be seen that, since the thickness $t_1$ of the weld nugget 5 is equal to the thickness $t_1$ of the weld nugget 3 (FIG. 1), the minimum phase value $\phi_{min1}$ of the resultant electromagnetic field intensity in testing the weld nugget 3 and weld nugget 5 (FIG. 2) will be the same, and hence the difference $l_1$ between $\phi_{max1}$ and $\phi_{min1}$ will be also the same.

Since the diameter $d_2$ of the weld nugget 5 of the test weld 6 is smaller than the diameter $d_1$ of the weld nugget 3 (FIG. 1) of the test weld 2, the distance $g_2$ (FIG. 2) within the limits where $\phi_{min1}$ has constant value, is smaller than $g_1$.

FIG. 3 shows a form of a spot weld wherein a weld nugget 8 of a test weld 9 has a thickness $t_2$ greater than the thickness $t_1$ of the weld nugget 3 (FIG. 1) of the test weld 2, and a diameter $d_1$ equal to the diameter of the weld nugget 3 of the test weld 2.

When the superimposed eddy current transducer 1 (FIG. 3) is displaced in the direction indicated by the arrow "a" between the points labelled "b" and "c", the phase angle between the resultant and primary magnetic fields will vary according to a curve 10. Referring to the curve 10, it could be seen that, since the thickness $t_2$ of the weld nugget 8 is greater than the thickness $t_1$ of the weld nugget 3 (FIG. 1), the minimum phase value $\phi_{min2}$ of the resultant electromagnetic field intensity in testing the weld nugget 8 (FIG. 3) will be smaller than the minimum phase value $\phi_{min1}$ of the resultant electromagnetic field intensity in testing the weld nugget 3 (FIG. 1), and hence the difference $l_2$ between $\phi_{max}$ and $\phi_{min2}$ will be greater than the difference $l_1$ between $\phi_{max}$ and $\phi_{min1}$.

Since the diameter $d_1$ of the weld nugget 8 (FIG. 3) of the test weld 9 is equal to the diameter $d_1$ of the weld nugget 3 (FIG. 1) of the test weld 2, the distance $g_1$ within the limits whereof $\phi_{min1}$ and $\phi_{min2}$ have constant value will be the same in testing the weld nugget 3 and weld nugget 8 (FIG. 3).

FIG. 4 shows a form of a spot weld wherein a test weld 11 has no weld nugget.

When the superimposed eddy current transducer 1 is displaced in the direction indicated by the arrow "a" between the points labelled "b" and "c", the phase angle between the resultant and primary magnetic fields remains constant according to a curve 12. This corresponds to a spot weld defect of "adhesion" type.

FIG. 5 shows a version with an air clearance 13 between welded parts 14, wherein a weld nugget is completely absent.

When the superimposed eddy current transducer 1 is displaced in the direction indicated by the arrow "a" between the points labelled "b" and "c", the phase angle between the resultant and primary magnetic fields will remain constant according to a curve 15, the phase value $\phi_{min3}$ being dependent upon the size of the air clearance 13.

An apparatus realizing the method described hereinabove comprises a sinusoidal voltage generator 16 having a reference channel connected to the output thereof and including a phase shifter 17 with its output connected to one of the inputs of a phase meter 18, and a measuring channel including an unbalanced bridge circuit 19 with the superimposed eddy current transducer 1 included into one of the branches thereof and complete with an attachment 20 for its mechanical displacement, and with its output connected to another input of the phase meter 18.

The phase meter 18 includes a phase detector 21 having the inputs connected to the outputs of preamplifiers 26, 27 through selective amplifiers 22, 23 and shapers 24, 25. The output of the phase shifter 17 is connected with the input of the preamplifier 27, and the output of the bridge circuit 19 is connected with the input of the preamplifier 26.

Connected to the output of the phase detector 21 is an input attenuator 28, the outputs of the attenuator 28 being connected to an indicator unit 29 and matching amplifier 30. Connected to one of the outputs of the matching amplifier 30 is a weld nugget diameter measuring channel 31 comprising a gating circuit 32 having its output connected to a weld nugget diameter indicator units 33. Connected to another output of the matching amplifier 30 is a weld nugget thickness measuring channel 34 comprising a maximum electric signal meter 35 having its output connected to a weld nugget thickness indicator unit 36. Connected to the third output of the matching amplifier 30 is a display unit 37 provided with a cathode-ray tube.

The attachment 20 for mechanical displacement of the superimposed eddy current transducer 1 comprises an electric motor 38 (FIG. 7) coupled with a reducer 39, the eddy current transducer 1 being fixed to an output rod 40 thereof.

The attachment 20 for mechanical displacement of the superimposed eddy current transducer 1 is mounted upon the test weld 2 on supports 41.

The apparatus realizing the method of non-destructive quality testing of spot welds operates as follows.

The superimposed eddy current transducer 1 is fixed to the output rod 40 of the reducer 39. The attachment 20 for mechanical displacement of the superimposed eddy current transducer 1 is mounted upon the test weld 2 on the supports 41.

Thereupon, the superimposed eddy current transducer 1 is started to move in the plane parallel to the surface of contact of welded parts so that, with displacement of the output rod 40, the superimposed eddy current transducer 1 would pass over the zone of the test weld 2 wherein the weld nugget 3 is absent and over the zone of the test weld 2 wherein the weld nugget 3 is present.

The sinusoidal voltage of the generator 16 (FIG. 6) is supplied to the phase shifter 17 which serves to set the phase of the reference voltage, and to the bridge circuit 19. As the superimposed eddy current transducer 1 is displaced with respect to the test weld 2, the phase of the output signal of the bridge circuit 19 varies in accordance with the position of the superimposed eddy current transducer 1 and with the weld quality.

The bridge circuit 19 is adjusted so that the phase of the output voltage is not dependent upon the size of the clearance between the superimposed eddy current transducer 1 and the test weld 2 and is determined only by variations in electric conductivity of the test zone which in turn is dependent upon the weld quality. From the output of the phase shifter 17, the signal is applied through the amplifier 27, selective amplifier 23, and shaper 25 to one of the inputs of the phase detector 21, and from the output of the bridge circuit 19 it is supplied through the preamplifier 26, selective amplifier 22, and shaper 24 to another input of the phase detector 21.

The preamplifiers 26 and 27 serve to increase the signal amplitude up to a required value. The selective amplifiers 22 and 23 are intended to decrease the effect of nonlinear signal distortions on the display of the apparatus. The shapers 24 and 25 shape the signal to trigger the phase detector 21, having steep edges the duration whereof is not dependent upon the amplitude of the output signal. From the phase detector 21, the signal proportional to variations in the phase of the output signal of the bridge circuit 19 is applied through the output attenuator 28 to the indicator unit 29 and matching amplifier 30. The output attenuator is intended to vary the sensitivity of the apparatus. The indicator unit 29 provides integral information on the dimensions of the weld nugget. The matching amplifier 30 is intended to match the output attenuator 28 with the display unit 37 with a cathode-ray tube, gating circuit 32, and maximum signal meter 35.

The display unit 37 with a cathode-ray tube performs time scanning of the signal, the distance between the maximum value and the minimum value of the signal defining the thickness of the weld nugget 3, and the distance within the limits in which the signal has its minimum value, defining the diameter of the weld nugget 3.

To determine the diameter of the weld nugget 3, the signal from the output of the matching amplifier 30 is applied to the gating circuit 32 which triggers under a definite level of the signal and outputs a square pulse, the pulse duration being proportional to the diameter of the weld nugget. From the output of the gating circuit 32, the signal is applied to the indicator unit 33 which measures the pulse duration and provides information on the diameter of the weld nugget 3.

To determine the thickness of the weld nugget 3, the signal from the output of the matching amplifier 30 is applied through the maximum signal meter 35 to the indicator unit 36 which provides information on the thickness of the weld nugget 3.

Thus, the proposed invention makes it possible to carry out continuous non-destructive quality testing of spot welds and to reveal such defects as reduction of the weld nugget diameter, reduction of the weld nugget thickness, adhesion, complete unfusion with an air clearance between welded parts.

Besides, the proposed invention makes it possible to perform testing without previous adjustment on a reference comparison weld and regardless of variations in the material chemical composition and environmental conditions, such as an ambient temperature.

What is claimed is:

1. A method of non-destructive quality testing of spot welds comprising the following steps of:
   (a) exposing a test weld nugget zone to a primary electromagnetic field to induce therein eddy currents, said eddy currents producing a secondary electromagnetic field which interacts with the primary electromagnetic field to form a resultant electromagnetic field;
   (b) displacing said primary electromagnetic field in a direction parallel to the surface of contact of the welded parts and between points located on either side of the test weld zone where the weld nugget is disposed;
   (c) measuring the phase angle between the resultant and primary electromagnetic fields at each of the points characterized by the maximum of the primary electromagnetic field and lying on the same line parallel to the surface of the welded junction being tested in the zone of the weld nugget, in the region disposed between the points located on either side of the weld junction being tested wherein the weld nugget is disposed, and establishing the maximum and minimum phase angle values;
   (d) evaluating the weld nugget thickness from the difference between the maximum phase angle value measured in the portion of the test weld zone where there is no weld nugget and the minimum phase angle value in the portion of the test weld zone where there is a weld nugget; and
   (e) evaluating the weld nugget diameter from the length of the zone within the limits in which the phase angle has its minimum value.

2. An apparatus for non-destructive quality testing of spot welds, comprising:
   (a) a sinusoidal voltage generator;
   (b) a reference channel having a phase shifter with its input connected to the output of said sinusoidal voltage generator;
   (c) a measuring channel having an unbalanced bridge circuit and having its input connected to the output of said sinusoidal voltage generator;
   (d) a phase meter having its inputs connected to the outputs of said phase shifter and unbalanced bridge circuit;
   (e) an eddy current transducer arranged in one of the branches of said unbalanced bridge circuit;
   (f) means for mechanically displacing said eddy current transducer in a plane parallel to the surface of contact of the welded parts;
   (g) means connected to said phase meter for measuring the thickness of a weld nugget; and
   (h) means connected to said phase meter for measuring the diameter of a weld nugget.

3. An apparatus as defined in claim 2, further comprising an attenuator connected between said phase meter and said measuring means.

4. An apparatus as defined in claim 3, further comprising a matching amplifier connected between said attenuator and said measuring means.

5. An apparatus as defined in claim 4, further comprising a display unit connected to said matching amplifier.

* * * * *